(12) United States Patent
Antoniou

(10) Patent No.: US 6,365,395 B1
(45) Date of Patent: Apr. 2, 2002

(54) PROCESS FOR REMOVING PROTEIN AGGREGATES AND VIRUS FROM A PROTEIN SOLUTION

(75) Inventor: Chris Antoniou, Chelmsford, MA (US)

(73) Assignee: Millipore Corporation

( * ) Notice: Subject to any disclaimer, the term of this patent is extended or adjusted under 35 U.S.C. 154(b) by 0 days.

(21) Appl. No.: 09/706,003

(22) Filed: Nov. 3, 2000

(51) Int. Cl.[7] .................................................. C12N 7/02
(52) U.S. Cl. ..................... 435/239; 435/235.1; 210/767; 210/805
(58) Field of Search ................................ 210/767, 805; 435/235.1, 239

(56) References Cited

U.S. PATENT DOCUMENTS 5,494,592 A * 2/1996 Latham, Jr. et al. ........ 210/805
5,630,946 A * 5/1997 Hart et al. .................. 210/805

FOREIGN PATENT DOCUMENTS

WO    WO 97 45140 A    12/1997
WO    WO 99 19343 A     4/1999

OTHER PUBLICATIONS

Lizen A et al "Separation and Quantitation of Monoclonal Antibody Aggregates by Asymmetrical Flow Filed–Flow Fractionation and Comparison to Gel Permeation Chromatography", Analytical Biochemicstry, US, Academic Press, San Diego, CA, vol. 212, 1993, pp. 469–480.

Luellau E et al "Development of a Downstream Process for the Isolation and Separation of Monoclonal Immunoglobulin A Monomers, Dimers and Polymers From Cell Culture Supernatant", Journal of Chromatography A, NL. Elsevier Science, vol. 796, No. 1, Feb. 13, 1998, pp. 165–175.

* cited by examiner

*Primary Examiner*—Jeffrey Stucker
(74) *Attorney, Agent, or Firm*—John Dana Hubbard; Paul J. Cook; Renato M. de Luna

(57) ABSTRACT

A process is provided for selectively removing protein aggregates and virus particles from a protein solution in a two-step filtration process. In a first step, a protein solution is filtered by tangential flow filtration through a cellulosic ultrafiltrate membrane at a transmembrane pressure of between about 1 and about 10 psi to produce a first permeate and a retentate stream. Water or aqueous buffer is added to the retentate stream to form an essentially constant volume retentate stream. The first permeate is filtered through a second ultrafiltration membrane to retain virus particles at a retention level of at least 3 LRV and to allow passage therethrough of a protein aggregate free and virus free protein solution.

13 Claims, 1 Drawing Sheet

PROCESS FOR REMOVING PROTEIN AGGREGATES AND VIRUS FROM A PROTEIN SOLUTION

BACKGROUND OF THE INVENTION

This invention relates to a process for selectively removing protein aggregates from a protein solution. More particularly, this is invention relates to a process for selectively removing protein aggregates and virus from a protein solution.

Protein solutions such as immunoglobulin protein (IgG) including polyclonal antibodies routinely contain protein aggregates comprising protein trimers or higher polymers. In order to administer this solution to a patient, it is necessary to first remove these aggregates to avoid a toxic response by the patient. When utilizing conventional filtration processes, aggregates are undesirable since the filter rapidly becomes plugged by the aggregates even at low aggregate concentrations of 0.1–0.2%. Accordingly, it has been necessary to utilize expensive gel chromatography or size exclusion chromatography processes to effect selective aggregate removal.

Virus also are a potential contaminant in parenteral and other solutions containing a protein which are derived from either whole organisms or mammalian cell culture sources. Currently several chemical and physical methods exist to inactivate virus. These methods are not generic to all virus equally and some operate at the expense of protein activity. For example, heat pasteurization is used in solutions where protein denaturization can be minimized through the addition of stabilizers. In the biotechnology industry, strategies have been adopted that combine several inactivation or removal steps in the downstream process to maximize virus removal capability and protein recovery. The operations used are generally those operations optimized to purify the parenteral product and are validated for the virus removal capability. Thus, virus removal is an additional capability from a by-product of normal operation. Finally, at the end of the process, steps such as chromatography, filtration or heat may be added to increase overall virus clearance. This strategy has two shortcomings; (1) the virus clearance of these operations may not apply to putative virus that cannot be assayed; and (2) the virus clearance of the process needs to be monitored continually. It is necessary to remove virus at a log retention value at least 3, i.e., at least about 99.9% removal.

Accordingly, it would be desirable to provide a process for removing protein aggregates from a protein solution by a filtration process which avoids premature plugging of the filtration membrane utilized in the process. In addition, it would be desirable to provide such a process which can be utilized in conjunction with a process for removing virus from the protein solution at a log retention value of at least 3.

SUMMARY OF THE INVENTION

The present invention provides a process for removing protein aggregates comprising protein dimers, protein trimers and higher protein polymers from a protein solution. The protein solution containing the aggregates are filtered through a cellulosic ultrafiltration membrane having a molecular weight cutoff between about 500 kD and about 1000 kD (the molecular weight of the solute that is 90% rejected by the membrane under low polarization conditions). The feed is filtered by tangential flow filtration wherein the feed is passed tangentially across the membrane surface to produce a retentate stream and a permeate stream. Filtration is effected using a transmembrane pressure between about 1 and about 10 psi. The retentate is recycled to a reservoir for the protein solution feed under conditions of essentially constant protein concentration in the feed by adding a buffer solution to the retentate. When filtering a protein solution containing virus, the filter utilized can retain virus particles. The filtration membrane is periodically washed with water or aqueous buffer to remove retained protein aggregates thereby to permit reuse of the membrane.

When utilizing a second filtration step to selectively retain virus, filtration can be effected with an ultrafiltration membrane either by tangential flow filtration (TFF) or by dead end (normal) filtration (NFF) wherein a permeate stream is produced while avoiding the formation of a retentate stream. The ultrafiltration membrane retains virus particles while permitting passage of protein monomer therethrough. When utilizing TFF, the retentate stream is recycled to a reservoir and then into contact with membrane(s) until substantially all of the protein is passed through the membrane. Subsequent to the filtration step, the membrane can be flushed with water or an aqueous buffer solution to recover any protein retained by the membrane.

The use of the two step process of this invention to remove protein aggregates and virus particles from a protein solution provides substantial advantages over the one step filtration process of the prior art. Since the membrane used in the first step of removing aggregates is washed with water, buffer or a cleaning agent to remove the retained aggregate, the membrane can be reused for the same purpose of removing protein aggregates from a protein solution. In addition, since the membrane utilized in the second step of removing virus particles does not foul with protein aggregates, its useful life is extended since it does not become plugged with protein aggregates.

DESCRIPTION OF SPECIFIC EMBODIMENTS

Figure 1:
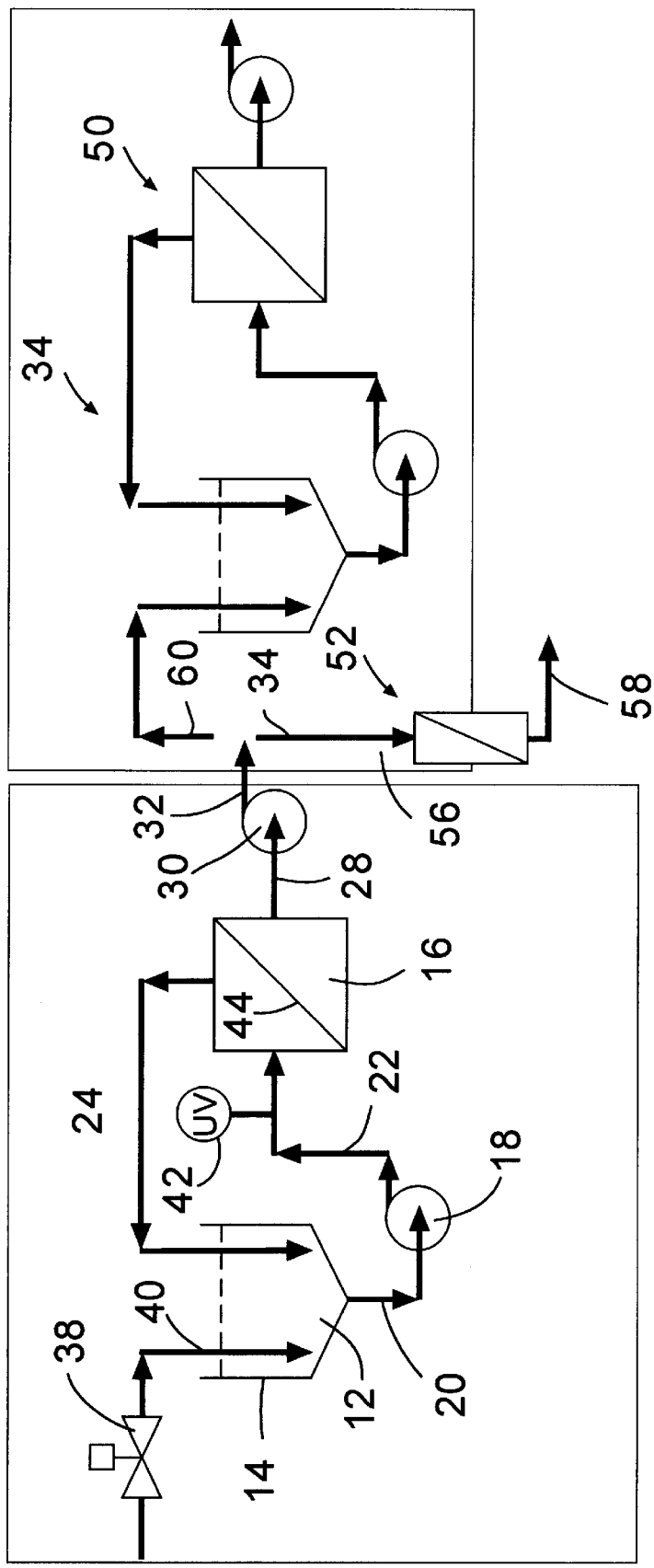
FIG. 1 is a flow diagram illustrating the process of this invention.

In accordance with this invention, a protein solution is first filtered with an ultrafiltration membrane to selectively retain protein aggregates comprising protein trimers and higher protein polymers while permitting passage of protein monomers therethrough. A portion of protein dimers in the protein solution are retained by the membrane while a portion of protein dimers in solution are passed through the membrane. This filtration step is effected under specific conditions utilizing a cellulosic ultrafiltration membrane having a molecular weight cutoff between about 500 and about 1000 kilodaltons (kD). Filtration is effected by tangential flow filtration (TFF) while utilizing a transmembrane pressure between about 1 and about 10 psi, preferably between about 1 and about 4 psi. When utilizing these conditions, substantially complete protein aggregate removal is effected while permitting recovery of greater than about 85% protein monomer, preferably greater than about 90% protein monomer.

Representative suitable cellulosic ultrafiltration membranes include those formed from regenerated cellulose such as or Vira Pure™ cellulosic ultrafiltration membranes available from Millipore Corporation, Bedford, Mass., USA. Filtration can be effected with one or a plurality of ultrafiltration membranes wherein the feed protein solution is contacted with the membrane in parallel flow.

When removing virus from a protein solution substantially free of protein aggregates, the permeate from the first membrane filtration step described above is directed to a second membrane filtration step. The second filtration step also utilizing one of more ultrafiltration membranes which can be conducted either in the TFF mode or the NFF mode. In either mode, the filtration is conducted under conditions to retain the virus generally having a 20 to 100 nanometer (nm) diameter on the membrane while permitting passage of protein monomer and a portion of protein dimer through the membrane. In addition, when filtration of the feed stream is completed, the membrane is flushed with water or an aqueous buffer solution to remove any retained proteins. The use of the flushing step permits obtaining high yield of protein solution substantially free of virus.

Representative suitable ultrafiltration membranes which can be utilized in the virus removal step include those formed from regenerated cellulose, polyethersulfone, polysulfone, polyimide, polyvinylidenedifluoride (PVDF) or the like.

The ultrafiltration membranes utilized in the process of this invention are characterized by a log retention value (LRV; the negative logarithm of the sieving coefficient) for virus particles and other, particles that increase monotomically with the diameter of the particle; in the size range of interest for virus of 20 to 100 nm diameter. Empirically, the LRV increases continuously with the size of the particle projected area (the square of the particle diameter). Where one is concerned with removing small sized virus particles from protein solution, satisfactory LRV of at least about 3 are obtained. However, the molecular weight cutoff is reduced thereby reducing protein recovery. Therefore, the user will choose a membrane which gives satisfactory LRV and protein recovery. In any event, the membranes utilized in the process of this invention are capable of producing an LRV for virus of 3 and can extend to as high as about 8 or greater where the virus particle size is between a 10 and 100 nm diameter. In addition, the virus removal membranes utilized in the process of this invention are characterized by a protein molecular weight cut off of between about 500 and 1000 kD. In all cases, the empirical relationship with particle projected area is retained. Log reduction values for virus particles (single solutes in solution; in absence of protein) depends upon the virus particle size. With small sized virus such as hepatitis an LRV of greater than about 3 can be obtained and with larger sized virus such as the AIDS virus, a LRV of greater than 6 can be obtain for example.

The following example illustrates the present invention and is not intended to limit the same.

EXAMPLE 1

Using a two-stage filtration system set forth in the drawing, to process a 3,000 liter 20 g.l IgG solution in 20 hours, the first stage requires 16 m² membrane area. Since the protein aggregate retained by this membrane is renewed by flushing with water or aqueous buffer after the filtration, its useful life is about one year. Assuming a target process cost for the virus removal at $ 1 per gram, the operating cost per gram for this first stage filtration is $0.064. With the addition of the second system to remove virus, only 10 m² filter area are required. The operating cost of the second stage is $0.71. Added together, the total operating cost is $0.77, a saving of 30%. When the IgG solution has a high monomer content (>94%), then normal flow filtration with a PVDF membrane such as a Vire solve 180 membrane available from Millipore Corporation, Bedford, Mass., USA can be used for the virus clearance stage. Assuming a mass flux of 525 gm/h, the operating cost of the second stage is $0.34 per gram and for both stages is $0.40 per gram; a saving of 60%.

|  | Stage 1 | Stage 2 (TFF) | Stage 2 (NFF) |
|---|---|---|---|
| Operating Mode: | ODS, TFF | Concentration + Flushing TFF | Concentration + Flushing NFF |
| Reusable Membranes: | Yes | No | No |
| Membrane Type: | ViraPure | ViraPure | V180 |
| Membrane Area | 16 m² | 10 m² | 10 m² |
| Rec. Flow Rate: | 160 lpm | 100 lpm |  |
| Permeate Flow Rate | 10 lpm | 10 lpm |  |
| Transmembrane Pressure | 1 to 2 PSI | 2 to 4 PSI | 15 PSI |
| Temperature: | 15° C. | 15° C. | 15° C. |
| Process Cost: | $0.064 per gram | $0.704 per gram | $0.34 per gram |
| Product Recovery: | 95% | 95% | 95% |
| 25 m NaCl Buffer | 2 × Initial Volume | <0.1 Initial Volume | <0.1 Initial Volume |

In the first stage 10 of the process of this invention, a protein solution 12 is retained by reservoir 14 and is pumped to TFF filtration unit 16 by pump 18 through conduits 20 and 22. The retentate is recirculated from filtration unit 16 to reservoir 14 through conduit 24. Permeate from the filtration unit is passed through conduit 28 by permeate pump 30 and through conduit 32 for processing in second stage 34. Essentially a constant volume in reservoir 14 is maintained by pumping aqueous buffer through valve 38 and conduit 40 into reservoir 14. The flow of buffer is controlled by measuring the protein concentration using an ultraviolet sensor 42 which regulates valve 38. By operating in this manner, protein aggregates are retained by membrane 44 while protein monomer is passed through membrane 44.

In the second stage 34, virus removal from the permeate protein solution can be effected either with a TFF system 50 or with an NFF system 52.

When utilizing the NFF system 52, permeate from the fist stage is directed from conduit 32, into conduit 54 and then into dead ended filtration unit 56. Substantially virus free protein solution is recovered through conduit 58.

When utilizing the TFF system 50, protein solution from conduit 42 is directed into conduit 60.

What is claimed is:

1. The process for selectively removing protein aggregates from an aqueous solution of proteins which comprises:

filtering by a tangential flow filtration step a protein solution containing said protein aggregate through an ultrafiltration membrane at a transmembrane pressure between about 1 and about 10 psi to produce a permeate stream comprising an aqueous solution of protein monomer, protein dimer and a retentate stream, adding an aqueous buffer solution to said retentate stream to retain a condition selected from the group consisting of (a) substantially constant volume of said retentate stream and (b) a substantially constant concentration of protein in said retentate stream and recycling said retentate having a substantially constant concentration to said tangential flow filtration step.

2. The process of claim 1 wherein said transmembrane pressure is between about 1 and about 4 psi.

3. The process of claim 1 including the additional step of flushing retained protein aggregate from said ultrafiltration membrane.

4. The process of claim 2 including the additional step of flushing retained protein aggregate from said ultrafiltration membrane.

5. The process for selectively removing protein aggregates and virus particles from an aqueous solution of proteins which comprises:

filtering by a tangential flow filtration step a protein solution containing said protein aggregates through a cellulosic ultrafiltration membrane at a transmembrane pressure between about 1 and about 10 psi to produce a permeate stream comprising an aqueous solution of protein monomer and a retentate stream, adding an aqueous solution to said retentate stream to retain a condition selected from the group consisting (a) a substantially constant volume of said a retentate stream and (b) a substantially constant concentration of protein in said retentate stream and recycling said retentate having a substantially constant volume to said tangential flow filtration step, filtering said permeate stream through a second ultrafiltration membrane having a molecular weight cut off of between about 500 kD and about 1000 kD to retain virus particles in said second ultrafiltrate membrane at a level of at least 3 LRV, and to form a second permeate stream comprising an aqueous, virus-free protein solution.

6. The process of claim 5 wherein said transmembrane pressure is between about 1 and about 4 psi.

7. The process of claim 5 including the additional step of flushing retained protein aggregate from said ultrafiltration membrane.

8. The process of claim 6 including the additional step of flushing retained protein aggregate from said ultrafiltration membrane.

9. The process of claim 6 which includes the further step of flushing retained protein from said second ultrafiltration membrane.

10. The process of claim 7 which includes the further step of flushing retained protein from said second ultrafiltration membrane.

11. The process of claim 8 which includes the further step of flushing retained protein from said second ultrafiltration membrane.

12. The process of claim 5 wherein filtration with said second ultrafiltration membrane is effected by tangential flow filtration.

13. The process of claim 5 wherein filtration with said second ultrafiltration membrane is effected by dead end flow filtration.

* * * * *